United States Patent [19]
Hammerstedt et al.

[11] Patent Number: 6,100,378
[45] Date of Patent: Aug. 8, 2000

[54] ENHANCEMENT OF THE PRO-FERTILITY ACTION OF A MOLECULE INVOLVED IN A SPERM-EGG BINDING

[75] Inventors: Roy H. Hammerstedt, Boalsburg; Surinder P. S. Gill, State College, both of Pa.; Rupert P. Amann, Ft. Collins, Colo.

[73] Assignee: BioPore, Inc., State College, Pa.

[21] Appl. No.: 09/268,070

[22] Filed: Mar. 12, 1999

Related U.S. Application Data

[60] Provisional application No. 60/077,713, Mar. 12, 1998.

[51] Int. Cl.⁷ ........................ C07K 14/52; G01N 35/567; C12N 5/00
[52] U.S. Cl. .......................... 530/324; 435/7.21; 800/21
[58] Field of Search .......................... 530/324; 435/7.21; 800/21

[56] References Cited

U.S. PATENT DOCUMENTS

| | | | |
|---|---|---|---|
| 5,571,787 | 11/1996 | O'Brien et al. | 514/2 |
| 5,696,080 | 12/1997 | O'Brien et al. | 514/2 |
| 5,700,909 | 12/1997 | O'Brien | 530/326 |

FOREIGN PATENT DOCUMENTS 9725620  7/1997  WIPO .

OTHER PUBLICATIONS

Barbato et al., "A practical in vitro sperm–egg binding assay that detects subfertile males". Biol Reprod. vol. 58 (1998), pp. 686–699.

Tajima et al., "Estimation of the relative fertilizing ability of frozen chicken spermatozoa using a heterospermic competition method", J. Reprod. Fert. 85 (1989), pp. 1–5.

Sylvester et al., "A Sulfated Glycoprotein Synthesized by Sertoli Cells and by Epididymal Cells in a Component of the Sperm Membrane", Biol. of Reprod. 31 (1984), pp. 1087–1101..

Igdoura et al., "Nonciliated Cells of the Rat Efferent Ducts Endocytose Testicular Sulfated Glycoprotein–1 (SGP–1) and Synthesize SGP–1 Derived Saposins", The Anatomical Record, 235 (1993), pp. 411–424.

Hiraiwa et al., Isolation, Characterization, and Proteolysis of Human Prosaposin, the Prescursor of Saposins (Sphingolipid Activator Proteins), Archives of Biochemistry and Biophysics, vol. 304, No. 1, (1993), pp. 110–116.

Azuma et al., "Cloning, expression and map assignment of chicken prosaposin", Biochem. J. 330 (1998), pp. 321–327.

Amann et al., "In Vitro Evaluation of Sperm Quality: An Opinion", Journal of Andrology, vol. 14, No. 6, (1993), pp. 397–406.

Hermo et al., "Immunocytochemical Localization of Sulfated Glycoprotein–1 (SGP–1) and Identification of Its Transcripts in Epithelial Cells of the Extratesticular Duct System of the Rat", The Anatomical Record, 232 (1992), pp. 401–422.

Igdoura et al., "Role of Sulfated Glycoprotein–1 (SGP–1) in the Disposal of Residual Bodies by Sertoli Cells of the Rat", Molecular Reproduction and Development, 40 (1995), pp. 91–102.

Munford et al., "Saposin–like proteins (SAPLIP) carry out diverse functions on a common backbone structure", Journal of Lipid Research 36 (1995), pp. 1653–1662.

Rosenthal et al., "Hormonal Regulation of Sulfated Glycoprotein–1 Synthesis by Nonciliated Cells of the Efferent Ducts of Adult Rats", Molecular Reproduction and Development, 40 (1995), pp. 69–83.

Sylvester et al., "Sulfated Glycoprotein–1 (Saposin Precursor) in the Reproductive Tract of the Male Rat", Biology of Reproduction, 41 (1989), pp. 941–948.

Doi et al., "Characterization of human endothelin B receptor and mutant receptors expressed in insect cells", Eur. J. Biochem, 248 (1997), pp. 139–148.

Roa et al., "High–Level Expression of Ovine Growth Hormone in *Escherichia coli*: Single–Step Purification and Characterization", Protein Expression and Purification, 11 (1997), pp. 201–208.

Tang et al., "Overexpression in *Escherichia coli* and Affinity Purification of Chick Kidney Ferredoxin", The Journal of Biological Chemistry, 268, No. 7, pp. 5069–5076, 1993.

Ledent et al., "Unexpected influence of a C–terminal–fused His–tag on the processing of an enzyme and on the kinetic and folding parameters", FEBS Letters, 413 (1997), pp. 194–196.

Gill et al., "Cryopreservation of Rooster Semen in Thirteen and Sixteen percent Glycerol", Poultry Science, 75 (1996), pp. 254–255.

Tajima et al., "Estimation of the relative fertility ability of frozen chicken spermatozoa using a heterospermic competition method", J. Reprod. Fert., 85 (1989), pp. 1–5.

(List continued on next page.)

*Primary Examiner*—Christopher S. F. Low
*Assistant Examiner*—Abdel A. Mohammed
*Attorney, Agent, or Firm*—Webb Ziesenheim Logsdon Orkin & Hanson, P.C.

[57] ABSTRACT

A synthetic peptide with enhanced pro-fertility action was produced by inclusion of additional amino acids at the carboxyl end of a previously disclosed synthetic peptide. Improvement in bioactivity over the previously disclosed peptide was demonstrated. A direct comparison of an earlier known synthetic peptide and an extended peptide involved brief exposure of sperm in vitro to one or the other peptide at several concentrations. When sperm then were evaluated in vitro using an egg-membrane substrate, an increased percentage of sperm bound for cells exposed to the new extended peptide. Similarly, when fertility of sperm after artificial insemination was the criterion, a greater percentage of eggs was fertilized by sperm exposed to the new extended peptide. In one preferred embodiment, this enhanced pro-fertility action was achieved with a peptide having a 68 amino acid sequence (SEQ ID NO 1:): Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Agr-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys-Val-Asn-His-His-His-His-His-His.

1 Claim, 2 Drawing Sheets

OTHER PUBLICATIONS

Hammerstedt et al., "Evaluation of sperm quality: Identificaiton of the subfertile male and courses of action", Animal Reproduction Science, 42 (1996), pp. 77–87.

Collard et al., "Biosynthesis and Molecular Cloning of Sulfated Glycoprotein 1 Secreted by Rat Sertoli Cells: Sequence Similarity with the 70–Kilodalton Precursor to Sulfatide/$G_{M1}$ Activator", Biochemistry, 27 (1998), pp. 4557–4564.

O'Brien et al., "Saposin proteins: structure, function, and role in human lysosomal storage disorders", The FASEB Journal 5, (1991), pp. 301–308.

Kishimoto et al., "Saposins: structure, function, distribution, and molecular genetics", Journal of Lipid Research 33, (1992), pp. 1255–1267.

SEQUENCE LISTING

<160> NUMBER OF SEQ ID NOS: 4

<210> SEQ ID NO 1
<211> LENGTH: 68
<212> TYPE: PRT
<213> ORGANISM: Unknown
<220> FEATURE:
<223> OTHER INFORMATION: varient of avian prosaposin

<400> SEQUENCE: 1

Cys Gln Ser Leu Gln Glu Tyr Leu Ala Glu Gln Asn Gln Arg Gln Leu
 1               5                  10                  15

Glu Ser Asn Lys Ile Pro Glu Val Asp Leu Ala Ala Val Val Ala Pro
            20                  25                  30

Phe Met Ser Asn Ile Pro Leu Leu Leu Tyr Pro Gln Asp Arg Pro Arg
        35                  40                  45

Ser Gln Pro Gln Pro Lys Ala Asn Glu Asp Val Cys Val Asn His His
    50                  55                  60

His His His His
65

<210> SEQ ID NO 2
<211> LENGTH: 69
<212> TYPE: PRT
<213> ORGANISM: Homo sapiens

<400> SEQUENCE: 2

Cys Glu Ser Leu Gln Lys His Leu Ala Glu Leu Asn His Gln Lys Gln
 1               5                  10                  15

Leu Glu Ser Asn Lys Ile Pro Glu Leu Asp Met Thr Glu Val Val Ala
            20                  25                  30

Pro Phe Met Ala Asn Ile Pro Leu Leu Leu Tyr Pro Gln Asp Gly Pro
        35                  40                  45

Arg Ser Lys Pro Gln Pro Lys Asp Asn Gly Asp Val Cys Val Asn His
    50                  55                  60

His His His His His
65

<210> SEQ ID NO 3
<211> LENGTH: 67
<212> TYPE: PRT
<213> ORGANISM: Avian

<400> SEQUENCE: 3

Cys Gln Ser Leu Gln Lys His Leu Ala Ala Met Lys Leu Gln Lys Gln
 1               5                  10                  15

Leu Gln Ser Asn Lys Ile Pro Glu Leu Asp Phe Ser Glu Leu Thr Ser
            20                  25                  30

Pro Phe Met Ala Asn Val Pro Leu Leu Leu Tyr Pro Gln Asp Lys Pro
        35                  40                  45

Lys Gln Lys Ser Lys Ala Thr Glu Asp Val Cys Val Asn His His His
    50                  55                  60

His His His
65

<210> SEQ ID NO 4
<211> LENGTH: 60
<212> TYPE: PRT

-continued

<213> ORGANISM: Avian

<400> SEQUENCE: 4

Cys Gln Ser Leu Gln Glu Tyr Leu Ala Glu Gln Asn Gln Arg Gln Leu
1               5                   10                  15

Glu Ser Asn Lys Ile Pro Glu Val Asp Leu Ala Arg Val Val Ala Pro
            20                  25                  30

Phe Met Ser Asn Ile Pro Leu Leu Leu Tyr Pro Gln Asp Arg Pro Arg
        35                  40                  45

Ser Gln Pro Gln Pro Lys Ala Asn Glu Asp Val Cys
    50                  55                  60

ENHANCEMENT OF THE PRO-FERTILITY ACTION OF A MOLECULE INVOLVED IN A SPERM-EGG BINDING

This present application claims the benefit of U.S. Provisional Application Ser. No. 60/077,713, filed Mar. 12, 1998, entitled "Enhancement of the Pro-Fertility Action of a Molecule Involved in Sperm-Egg Binding."

BACKGROUND OF THE INVENTION

Related Applications

Subfertility is a major problem with domestic animals, humans and certain endangered species. Subfertility has a billion dollar impact on food production. In many circumstances, most sperm in a sample must have a low fertilizing potential despite normality of motion, morphology, or "viability" (plasma membrane excludes dye). This is evidenced in two ways. First, attributes of each spermatozoan other than "motility" and "viability" are important, and failure in one of many critical functions renders a spermatozoan incapable of fertilizing an oocyte (Amann and Hammerstedt, 1993; Hammerstedt, 1996). An in vitro sperm-binding assay (Barbato et al., 1998; Amann et al., 1999) allows detection of certain males ejaculating semen with a relatively low percentage of sperm capable of binding in this assay and, hence, likely to be of low fertility. Fertility trials confirm general correctness of the classification (Barbato et al., 1998).

Knowledge of sperm-associated proteins is evolving rapidly, and it is evident that sperm are exposed to, and modified by, specific proteins secreted at multiple sites within the testis and/or excurrent duct system. As summarized by Amann et al. (1999), individual glycosylated molecules have received emphasis in considerations of sperm-to-egg binding, at the potential risk of overlooking non-glycosylated molecules. Also, some authors rightly have highlighted the need for multiple and synergistic ligands. Hammerstedt et al. (1997) disclosed a novel native protein and several non-glycosylated, synthetic peptides which, when included in buffer suspending sperm, increased the percentage of sperm bound using an in vitro assay and also increased fertility of sperm used for artificial insemination. The native peptide is thought to be formed from prosaposin.

Full-length, unprocessed prosaposin (Collard et al., 1988; O'Brien and Kishimoto, 1991; Kishimoto et al., 1992; Azuma et al., 1998) also has been termed sulfated glycoprotein 1 or SGP-1. Conventionally, prosaposin is proteolytically processed (Hiraiwa et al., 1993) into 4 saposins (A, B, C and D; each 13 to 15 kD) and 3 intervening segments (A–B, B–C and C–D; each 6 to 8 kD). Saposins are considered to be activator proteins increasing the catalytic rate of lipid-modifying enzymes, as in lysosomes (O'Brien and Kishimoto, 1991; Kishimoto et al., 1992; Mumford et al., 1995). Until Hammerstedt et al. (1997), no function had been ascribed to any of the 3 intervening segments. Prosaposin (or mature products thereof) is produced throughout the body although not secreted by most tissues (Collard et al., 1988; Kishimoto et al., 1992; Sylvester et al., 1984, 1989; Igdoura et al., 1993; Rosenthal et al., 1995).

The antibody commonly used to localize prosaposin apparently binds an epitope(s) common to each of the 4 saposins (Igdoura et al., 1993; Igdoura and Morales, 1995) and, hence, also is bound by prosaposin. Based on probing of western blots with antibody, prosaposin (and traces of saposins) was found in luminal fluids in the excurrent ducts conveying sperm from the testes (Sylvester et al., 1989; Igdoura and Morales, 1995), but there was a complete absence of sperm-labeling throughout the excurrent ducts (Sylvester et al., 1989; Hermo et al., 1992).

The most favored synthetic peptides of Hammerstedt et al. (1997) are a sequence integral to a truncated portion of the rat or human prosaposin molecule extending from the cystine amino acid near the distal terminus of saposin A, through the intervening sequence between saposin A and saposin B., and through the proximal cystine amino acid in saposin B; a total of sixty (60) amino acids in rat or sixty-one (61) amino acids in human. Hammerstedt et al. (1997) further claim that maximum activity is obtained by linking the terminal cystine amino acids in most favored disclosed sequences by a disulfide bond, to provide a hairpin form.

SUMMARY OF THE INVENTION

In the course of advancing technology disclosed by Hammerstedt et al. (1997) we had reason to have chemically synthesized a novel sequence which: (1) departs from and adds to a prior art sequence of Hammerstedt et al. (1997) (SEQ ID NO: 4 herein) ; and (2) incorporates an amino acid sequence not found in the corresponding portion of the prosaposin molecule. This sequence is presented as SEQ ID NO: 1. The analogous new sequences in human and chicken prosaposin are presented as SEQ ID NO: 2 and SEQ ID NO: 3.

The first new sequence (SEQ ID NO: 1) totals 68 amino acids and is: Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Agr-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys-Val-Asn-His-His-His-His-His-His (reading, first to last, from $NH_2$ to COOH)

The second new sequence (SEQ ID NO: 2) totals 69 amino acids and is: Cys-Glu-Ser-Leu-Gln-Lys-His-Leu-Ala-Glu-Leu-Asn-His-Gln-Lys-Gln-Leu-Glu-Ser-Asn-Lys-Ile-Pro-Glu-Leu-Asp-Met-Thr-Glu-Val-Val-Ala-Pro-Phe-Met-Ala-Asn-Ile-Pro-Leu-Leu-Leu-Tyr-Pro-Gln-Asp-Gly-Pro-Arg-Ser-Lys-Pro-Gln-Pro-Lys-Asp-Asn-Gly-Asp-Val-Cys-Val-Asn-His-His-His-His-His-His (reading, first to last, from $NH_2$ to COOH)

The third new sequence (SEQ ID NO: 3) totals 67 amino acids and is: Cys-Gln-Ser-Leu-Gln-Lys-His-Leu-Ala-Ala-Met-Lys-Leu-Gln-Lys-Gln-Leu-Gln-Ser-Asn-Lys-Ile-Pro-Glu-Leu-Asp-Phe-Ser-Glu-Leu-Thr-Ser-Pro-Phe-Met-Ala-Asn-Val-Pro-Leu-Leu-Leu-Tyr-Pro-Gln-Asp-Lys-Pro-Lys-Gln-Lys-Ser-Lys-Ala-Thr-Glu-Asp-Val-Cys-Val-Asn-His-His-His-His-His-His (reading, first to last, from $NH_2$ to COOH)

A prior art sequence (SEQ ID NO: 4) considered in comparison in Example 2 totals 60 amino acids and is: Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Arg-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys (reading, first to last, from $NH_2$ to COOH)

DETAILED DESCRIPTION OF THE INVENTION

Figure 1:
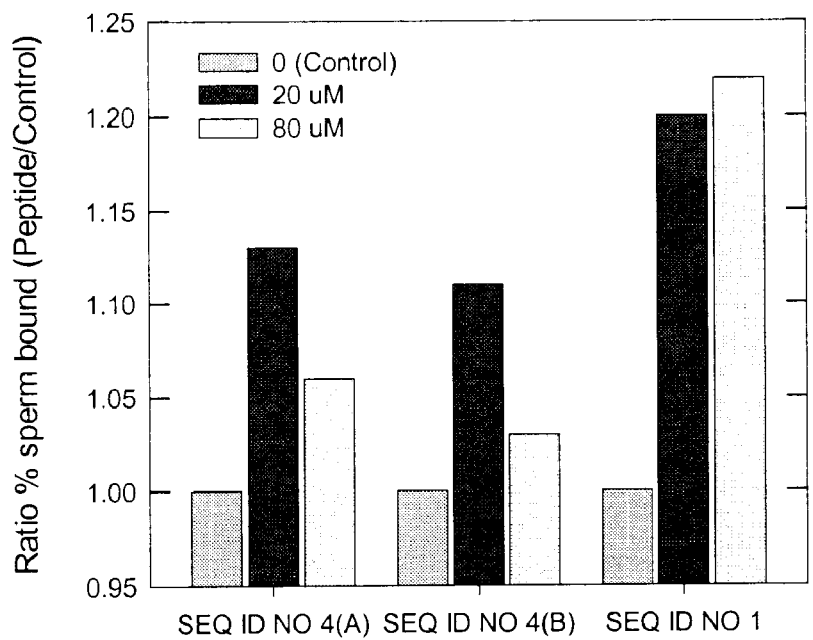
FIG. 1 shows in graphic form the mean ratio comparing percentage of frozen-thawed rooster sperm bound to an egg-membrane substrate for peptide-treated v. control aliquots of the same seminal samples. All three peptides were incubated at 0, 20 and 80 ng peptide/million sperm prior to evaluation. Ration % bound calculated as: % bound with Peptide / % bound for Control.

In the course of advancing technology disclosed by Hammerstedt et al. (1997) we had reason to have chemically synthesized a novel sequence which: (1) departs from and adds to SEQ ID #12 of Hammerstedt et al. (1997); and (2) incorporates an amino acid sequence not found in the corresponding portion of the prosaposin molecule. This sequence is presented as SEQ ID NO: 1. The analogous new sequences in human and chicken prosaposin are presented as SEQ ID NO: 2 and SEQ ID NO: 3.

The first new sequence (SEQ ID NO: 1) totals 68 amino acids and is: Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Agr-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys-Val-Asn-His-His-His-His-His-His (reading, first to last, from NH$_2$ to COOH).

The second new sequence (SEQ ID NO: 2) totals 69 amino acids and is: Cys-Glu-Ser-Leu-Gln-Lys-His-Leu-Ala-Glu-Leu-Asn-His-Gln-Lys-Gln-Leu-Glu-Ser-Asn-Lys-Ile-Pro-Glu-Leu-Asp-Met-Thr-Glu-Val-Val-Ala-Pro-Phe-Met-Ala-Asn-Ile-Pro-Leu-Leu-Leu-Tyr-Pro-Gln-Asp-Gly-Pro-Arg-Ser-Lys-Pro-Gln-Pro-Lys-Asp-Asn-Gly-Asp-Val-Cys-Val-Asn-His-His-His-His-His-His (reading, first to last, from NH$_2$ to COOH)

The third new sequence (SEQ ID NO: 3) totals 67 amino acids and is: Cys-Gln-Ser-Leu-Gln-Lys-His-Leu-Ala-Ala-Met-Lys-Leu-Gln-Lys-Gln-Leu-Gln-Ser-Asn-Lys-Ile-Pro-Glu-Leu-Asp-Phe-Ser-Glu-Leu-Thr-Ser-Pro-Phe-Met-Ala-Asn-Val-Pro-Leu-Leu-Leu-Tyr-Pro-Gln-Asp-Lys-Pro-Lys-Gln-Lys-Ser-Lys-Ala-Thr-Glu-Asp-Val-Cys-Val-Asn-His-His-His-His-His-His (reading, first to last, from NH$_2$ to COOH)

A prior art sequence (SEQ ID NO: 4) considered in comparison in Example 2 totals 60 amino acids and is: Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Arg-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys (reading, first to last, from NH$_2$ to COOH).

SEQ ID NO: 1 was prepared in anticipation that the six histidine tail would facilitate binding to a Ni-column. Although we have not tested that feature of SEQ ID NO: 1, SEQ ID NO: 2, or SEQ ID NO: 3, we have evaluated bioactivity of SEQ ID NO: 1. We have found, as did Barbato et al. (1998), that in vitro binding of sperm to an egg membrane substrate is diagnostic of fertilizing potential of sperm in that seminal sample. Hence, we compared the increase in binding of rooster sperm induced by brief exposure to selected concentrations of a prior art peptide of Hammerstedt el al. (1997), known to be bioactive in vitro, with similar concentrations of SEQ ID NO:- 1 and, unexpectedly, we found that the benefit from SEQ ID NO: 1 was substantially greater. There was a greater increase in percent sperm bound and a wider range in effective concentrations.

Subsequently, we conducted a fertility trial using frozen-thawed rooster sperm exposed to SEQ ID NO: 1 versus a prior art peptide. Again, to our surprise, we found that the peptide of SEQ ID NO: 1 had greater bioactivity than the prior art peptide, in terms of both increasing the percentage of eggs laid which were fertilized and in having a wider range of effective concentrations. Hence, it appears that with SEQ ID NO: 1 careful control of the molar concentration, or mass of peptide per billion sperm, is far less critical than with the peptide of the prior art. This should facilitate actual use in the field. Most importantly, the likely increase in number of young hatched (poultry) or born (mammals) would be greater.

Based on fertility trials with chickens, turkeys and cattle using a preferred peptide disclosed in the prior art, we obtained results similar to those of Hammerstedt et al. (1997), as we also have using the same sperm-binding assay with bull, horse, human, mouse and pig sperm. Hence, we anticipate that SEQ ID NO: 1 will be equally advantageous with these species as it is with chickens.

The peptide represented by SEQ ID NO: 1 differs from those of the prior art by extension of the COOH end. This extension consists of two possibly irrelevant amino acids plus six histidine amino acids. The corresponding eight amino acids in rat prosaposin are: Gln-Asp-Cys-Met-Lys-Leu-Val-Thr. The corresponding eight amino acids in human prosaposin are: Gln-Asp-Cys-Ile-Gln-Met-Val-Thr. The corresponding eight amino acids in chicken prosaposin are: Gln-Asp-Cys-Ile-Arg-Leu-Val-Thr. None of these sequences is similar to the addition used in SEQ ID NO: 1, namely: Val-Asn-His-His-His-His-His-His. Hence, knowledge of the prosaposin molecule would not logically have led to addition of these amino acids. However, we anticipate that insertion of two to six irrelevant amino acids between the cysteine and first histidine, rather than the Val-Asn of SEQ ID NO: 1, or incorporation of a repeat of seven or eight rather than six histidine amino acids would similarly improve over the prior art. Further, we speculate that addition of a repeat of six to eight histidine amino acids, with a spacer of two to six irrelevant amino acids, to the cysteine amino acid on the NH$_2$ terminus of prior art peptides, rather than to the COOH end, also might enhance bioactivity.

SEQ ID NO: 1 also differs from another prior art peptide of Hammerstedt et al. (1997) which, although substantially shorter than SEQ ID NO: 1, extended nine amino acids in the COOH direction beyond the terminal cystine. This prior art peptide had essentially no bioactivity (Hammerstedt et al., 1997). Hence, knowledge of the other sequences disclosed and tested by Hammerstedt et al. (1997) would not logically have led to addition of these amino acids.

Finally, the extension on the COOH end which distinguishes SEQ ID NO: 1 from the first above mentioned prior art peptide of Hammerstedt et al. (1997), namely Val-Asn-His-His-His-His-His-His,was made because the histidine-repeat sequence is known to facilitate binding to a Ni-column. However, the literature on use of Ni-columns or histidine-repeat sequencesdoes not include the concept that a sequence such as Val-Asn-His-His-His-His-His-His would increase the pro-fertility action of a parent peptide. There appears to be no prior art or basis for the observed effects.

EXAMPLE 1

We used the BioPore® Sperm-Binding Assay (Amann et al., 1999) to compare. percentage of sperm binding to an egg-membrane substrate (similar to Barbato et al., 1998) after brief in vitro exposure to three concentrations of a prior art peptide (Hammerstedt et al., 1997), representing each of two lots of peptide SEQ ID NO: 4 (after disulfide linking the cystine residues) or three concentrations of SEQ ID NO: 1

(after disulfide linking the cystine residues). Briefly, cryopreserved rooster semen (Gill et al., 1996) from broiler males (Barbato et al., 1998) was thawed, deglycerolated (Gill et al., 1996), and adjusted to provide a concentrated suspension of sperm in an appropriate salts buffer. We used one containing: 0.600 g sodium glutamate, 0.210 g potassium glutamate, 0.100 g glucose, 0.070 g sorbitol, 0.035 g magnesium sulfate, 0.210 g potassium acetate, 0.050 g potassium citrate, 0.700 g di-potassium phosphate, 0.160 g mono-potassium phosphate, 0.800 g di-sodium phosphate, 0.100 9 potassium hydroxide, 0.300 g N,N -bis[2-hydroxyethyl]-2-aminoethanesulfonic acid, 0.400 g N-[2-hydroxyethyl]piperazine-N'-[2-ethanesulfonic acid], and 0.400 g N-tris[hydroxymethyl]methyl-2-aminoethanesulfonic acid, dissolved in distilled water to make 100 ml (Tajima et al., 1989). Aliquots of this suspension were placed in tubes containing one of the three peptide sequences at 0, 20 or 80 ng per million sperm. After mixing and 10 minutes incubation at 37° C., the suspensions were further diluted and assayed using 2 million sperm/well in the microwell assay plates. Plates were incubated at 32° C. for 60 min, after which unbound sperm were decanted, the wells washed, and the DNA in sperm bound to the egg-membrane substrate in the microwell plates quantified (Barbato et al., 1998). Resultant data (FIG. 1) revealed that for the 2 preparations of SEQ ID NO: 4 maximum benefit was at 20 ng/million sperm; binding was 1.13 and 1.17× the value for the non-peptide control. With SEQ ID NO: 1, however, binding for suspensions exposed to either 20 or 80 ng/million sperm was greater, namely 1.20 and 1.22 the control value.

EXAMPLE 2

Figure 2:
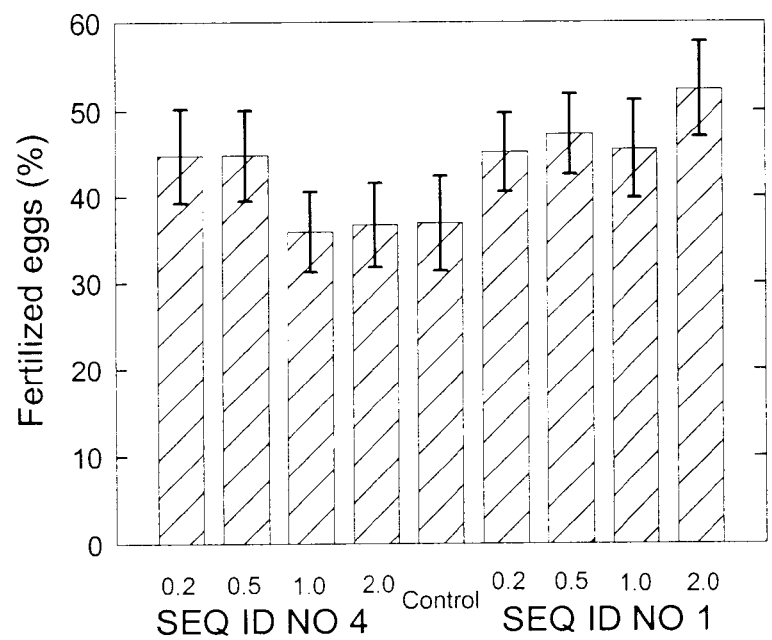
FIG. 2 shows in graphic form the mean percentage of fertilized eggs laid by hens inseminated four times at 4-day intervals with a limited number of frozen-thawed rooster sperm exposed to 0.2, 0.5, 1.0 or 2.0 μM SEQ ID NO: 4 (left); untreated control sperm (center); or 0.2, 0.5, 1.0 or 2.0 μM SEQ ID NO 1 (right). Each bar based on >425 eggs.

To compare fertility achieved after exposure of rooster sperm to SEQ ID NO: 4 and SEQ ID NO: 1, we used cryopreserved semen as in Example 1. To facilitate detection of benefit from peptides, we used a limited number of sperm for each artificial insemination. Pooled, deglycerolated semen (1 billion sperm/ml; at 0–4C.), in salts buffer as described in Example 1, was dispensed into tubes containing SEQ ID NO: 4 or SEQ ID NO: 1 to make nine suspensions: 0.0 (control), 0.2, 0.5, 1.0 or 2.0 $\mu$M and mixed. Artificial insemination of White Leghorn hens (40/group) was within 1 hour, and used 50 $\mu$l (50 million sperm). Eggs were collected daily, stored $\leq$7 d at 14C., incubated, and candled on day 7 (eggs with viable embryo were classed as fertile). Data resulting from four inseminations at 4-day intervals are shown (FIG. 2). It was concluded that both 0.2 and 0.5 $\mu$M SEQ ID NO: 4 improved fertility as did 0.2, 0.5, 1.0 and 2.0 $\mu$M SEQ ID NO: 1. Hence, SEQ ID NO: 4 was of benefit over a narrow ~2.5-fold range (0.2 to 0.5 $\mu$M) where as SEQ ID NO: 1 was of benefit over a $\geq$10- fold range (0.2 to 2.0 $\mu$M). The increase in fertility (above the control value) with the best concentration of SEQ ID NO: 1 (15.4 units at 2.0 $\mu$M) was 2.0× that with SEQ ID NO: 4 (7.8 units at 0.5 $\mu$M). Clearly, brief in vitro exposure of sperm to SEQ ID NO: 1 rather than SEQ ID NO: 4 before artificial insemination gave a greater increase in percentage of fertilized eggs over a greater range in concentration.

Literature Cited

Amann R P and Hammerstedt R H (1993), "In vitro evaluation of sperm quality: an opinion," *J Andrology* 14:397–406.

Amann R P, Hammerstedt R H and Shabanowitz R B (1999), "Exposure of human, bull or boar sperm to a synthetic peptide increases binding to an egg-membrane substrate" *J Androloqy* 20:34–41.

Azuma N, Seo H-C, Lie ø,F Y Q, Gould R M, Hiraiwa M, Burt D W, Patton I R, Morrices D R, O'Brien J S and Kishimoto Y (1998), "Cloning, expression and map assignment of chicken prosaposin," *Biochem J* 330:321–327.

Barbato G F, Cramer P G and Hammerstedt R H (1998), "A practical in vitro sperm-egg binding assay that detects subfertile males," *Biol Reprod* 58:686–699.

Collard M W, Sylvester S R, Tsuruta J K and Griswold M D (1988), "Biosynthesis and molecular cloning of sulfated glycoprotein-1 secreted by rat Sertoli cells: sequence similarity with the 70-kilodalton precursor to sulfatide/GM 1 activator," *Biochemistry* 27:4557–4564.

Hammerstedt R H (1996), "Evaluation of sperm quality: Identification of the subfertile male and courses of action," *Anim Reprod Sci* 42:77–87.

Hammerstedt R H, Cramer P G and Barbato G F (1997), "A method and use of polypeptide in sperm-egg binding to enhance or decrease fertility," International Patent Publication Number WO/97/25620. 41 pp.

Hermo L, Morales C and Oko R (1992), "Immunocytochemical localization of sulfated glycoprotein-1 (SGP-1) and identification of its transcripts in epithelial cells of the extratesticular duct system of the rat," *Anat Rec* 232:401–422.

Hiraiwa M, O'Brien J S, Kishimoto Y, Galdzicka M, Fluharty A L, Ginns E I and Martin D M (1993), *Arch Biochem Biophys* 302:110–116.

Igdoura S A and Morales C R (1995), "Role of sulfated glycoprotein-1 (SGP-1) in the disposal of residual bodies by Sertoli cells of the rat," *Mol Reprod Dev* 40:91–102.

Igdoura S A, Hermo L, Rosenthal A and Morales C R (1993), "Nonciliated cells of the rat efferent ducts endocytose testicular sulfated glycoprotein-1 (SGP-1) and synthesize SGP-1 derived saposins," *Anat Rec* 235:411–424.

Kishimoto Y, Hiraiwa M and O'Brien J S (1992), "Saposins: structure, function, distribution, and molecular genetics," *J Lipid Res* 33;1255–1267.

Munford R S, Sheppard P O and O'Hara P J (1995), "Saposin-like proteins (SAPLP) carry out diverse functions on a common backbone structure," *J Lipid Res* 36;1653–1663.

O'Brien J S and Kishimoto Y (1991), "Saposin proteins: structure, function, and role in human lysosomal storage disorders," *FASEB J* 5:301–308.

Rosenthal A L, Igdoura S A, Morales C R and Hermo L (1915), "Hormonal regulation of sulfated glycoprotein-1 synthesis by nonciliated cells of the efferent ducts of adult rats," *Mol Reprod Dev* 40:69–83.

Sylvester S R, Skinner M K and Griswold M D (1984), "A sulfated glycoprotein synthized by Sertoli cells and by epididymal cells is a component of the sperm membrane," *Biol Reprod* 31:1087–1101.

Sylvester S R, Morales C, Oko R and Griswold M D (1989), "Sulfated glycoprotein-1 (saposin precursor) in the reproductive tract of the male rat," *Biol Reprod* 41:941–948.

Gill S P S, Buss E G and Mallis R J (1996), "Cryopreservation of rooster semen in thirteen and sixteen percent glycerol," *Poultry Sci* 75:254–256.

Tajima A, Graham E F and Hawkins D M (1989), "Estimation of the relative freezing ability of frozen chicken spermatozoa using heterospermic competition method," *J Reprod Fertil* 85:1–5.

We claim:

1. A peptide for enhancing sperm-egg binding having the amino acid sequence consisting substantially as set forth in SEQ ID NO: 1, SEQ ID NO: 2, or SEQ ID NO: 3.

\* \* \* \* \*

UNITED STATES PATENT AND TRADEMARK OFFICE
CERTIFICATE OF CORRECTION

PATENT NO. : 6,100,378
DATED : August 8, 2000
INVENTOR(S) : Roy H. Hammerstedt et al.

It is certified that error appears in the above-identified patent and that said Letters Patent is hereby corrected as shown below:

Column 4 Line 62 after "compare" delete period (.)

Column 5 Line 11 "0.100 9" should read --0.100 g--.

Column 9 Line 20, Claim 1, delete "substantially as set forth in" and insert --of--.

Signed and Sealed this

Twenty-fourth Day of April, 2001

Attest:

NICHOLAS P. GODICI

Attesting Officer

Acting Director of the United States Patent and Trademark Office